United States Patent [19]

Sheldon

[11] Patent Number: 4,650,459
[45] Date of Patent: Mar. 17, 1987

[54] CONVOLUTELY WOUND PAPER TAMPON TUBE

[75] Inventor: Donald A. Sheldon, Appleton, Wis.

[73] Assignee: Kimberly-Clark Corporation, Neenah, Wis.

[21] Appl. No.: 789,674

[22] Filed: Oct. 21, 1985

[51] Int. Cl.⁴ ............................................. A61F 13/20
[52] U.S. Cl. .................................................. 604/15
[58] Field of Search ................ 604/11, 13, 14, 15–18, 604/904

[56] References Cited

U.S. PATENT DOCUMENTS

| 3,015,332 | 1/1962 | Brecht | 604/15 |
| 3,170,489 | 2/1965 | Cunningham | 138/145 |
| 3,194,275 | 7/1965 | Biggs | 138/144 |
| 3,429,312 | 2/1969 | Stump | 604/15 |
| 3,581,744 | 6/1971 | Voss | |
| 3,696,812 | 10/1972 | Jaycox | |
| 3,760,808 | 9/1973 | Bleuer | 604/14 |
| 4,508,531 | 4/1985 | Whitehead | 604/14 |
| 4,536,178 | 8/1985 | Lichstein et al. | 604/15 |

FOREIGN PATENT DOCUMENTS

| 128793 | 11/1946 | Australia | 604/15 |
| 2255879 | 7/1975 | France | 604/15 |
| 1049894 | 11/1966 | United Kingdom | |

Primary Examiner—John D. Yasko
Attorney, Agent, or Firm—P. A. Leipold; D. L. Traut; J. J. Duggan

[57] ABSTRACT

Inner and outer convolutely wound cardboard tubes of a tampon applicator are formed with a different number of ply windings.

5 Claims, 6 Drawing Figures

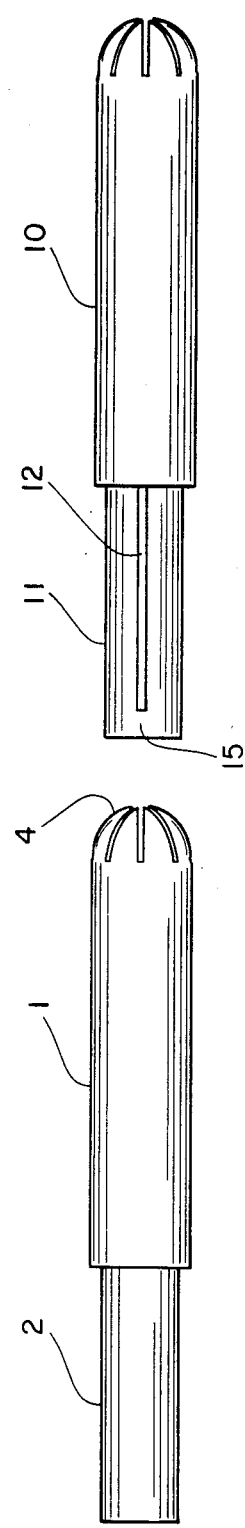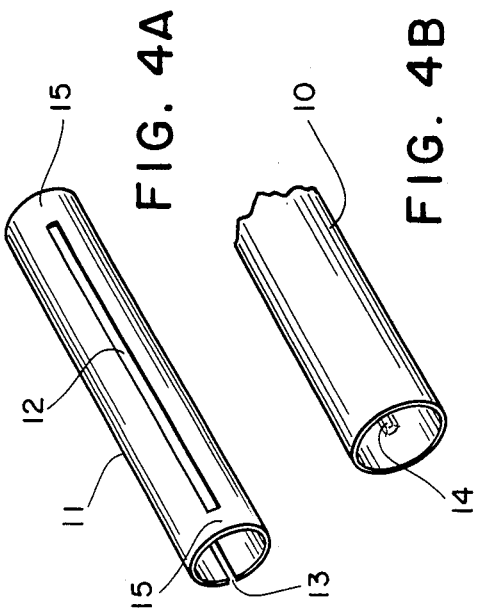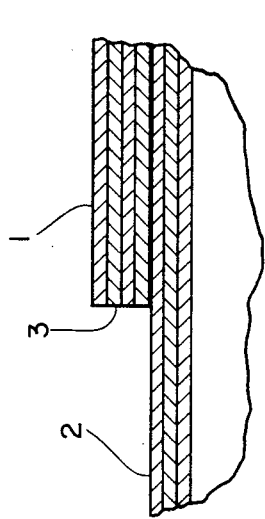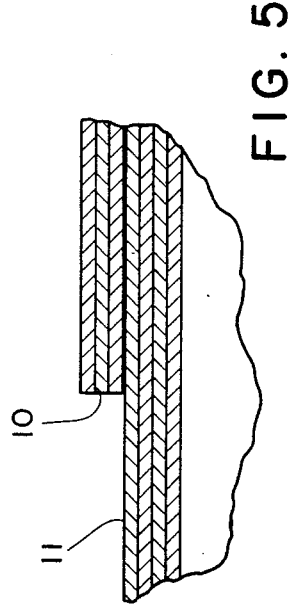

CONVOLUTELY WOUND PAPER TAMPON TUBE

TECHNICAL FIELD

The present invention relates, generally, to the field of catamenial tampons for personal feminine care or protection in order to absorb or otherwise contain menstrual fluids or similar exudate. The present invention relates more particularly to paper tubes particularly useful for the insertion of a tampon. Of special concern is a more economical construction of a plunger type tampon.

DESCRIPTION OF THE BACKGROUND ART

All manner and variety of devices or appliances configured for the absorption of such body fluids as menses are of course well known. As a class, these articles ought to possess certain necessary attributes of absorbency, comfort and psychological as well as physiological or physical protection. Desirably, these devices also are characterized as being discreet both during wear and when carried upon the wearer's person in anticipation of use. As will be seen from the ensuing discussion, these objectives are somewhat antagonistic in the sense that attainment of one has heretofore ordinarily necessitated compromising one or more other desirable feature.

The art has offered two basic types of feminine protection device with those objectives borne in mind; sanitary napkins or pads have been developed for external wear about the vulvar region of a user while tampons have been developed for residence within the vaginal cavity and interruption of menstrual flow therefrom. Each offers distinct advantages and, as one would expect, distinct or peculiar disadvantages, which range from psychological impediments and/or concerns to physical discomfiture.

Looking to tampons as such an alternative to sanitary napkins, the same are preferred by a substantial number of women. Offering the ability to intercept menses within the vaginal canal, the disadvantages inhering in sanitary napkins in respect of covers and attachment means are overcome by this approach. That is not to say, however, that tampons afford a superior means of feminine protection for all users. For example, there are many individuals who, for either physical or psychological reasons, are unable to utilize tampons as an effective means of feminine protection. Tampons themselves may be found lacking in terms of construction inasmuch as efficacy relies significantly on the ability of the same to undergo radial expansion upon fluid swelling in order to form a seal or zone of occlusion within the vaginal canal. Failure to do so implies overall failure of the tampon to serve as a reliable protection device.

While there are essentially three types of tampons, plunger, stick and digital, the most preferable type of tampon in the United States is the plunger type. The tubes for the plunger type are either of the disposable or non-disposable variety. During the past several decades, increasing emphasis has been placed upon the ease of disposability of consumer goods after the goods have performed their intended purpose. A paper tampon tube, to be easily disposable must be formed with an adhesive readily soluble in cold water and preferably constructed so that delamination of the tube occurs in a short period of time.

Plunger-type tampons are generally formed in two parts with an outer tube having an inner diameter slightly greater than the outer diameter of the tampon pledget inserted therein. The second part of a tampon inserter means is some type of plunger which operates in cooperation with the tube to expel the pledget. The tubes are generally made of paper products such as cardboard or thermoplastic. Further, thermoplastic tubes generally have an insertion end which forms a hemispherical profile around the leading edge of the tampon to protect it and maintain its integrity during insertion. Commercially available tampons utilizing cardboard tubes, however, generally do not have this type of closure, but rather the leading edge of the tampon extends beyond the tube end. Both thermoplastic and paper derived tubes can be made with a reduced diameter base which can be used for gripping or to better maintain the plunger used for expulsion, or for both purposes.

The ideal tampon tube should be inexpensive, simple to make, easily disposable, attractive and hygienic. Both molded plastic and paper inserter tubes have not been completely satisfactory in meeting these desirable attributes. There are no commercially available tubes molded from thermoplastics that are water disposable or flushable. Furthermore, the relative cost of thermoplastic is substantially greater than tubes which are made from paper or paper products. In addition, thermoplastic molded tubes having a hemispherical shaped leading edge comprising individual arcuate shaped lobes are extremely difficult to mold without providing lobes having sharp edges or flashing, i.e. irregularly shaped burrs of plastic. Such tubes could provide problems when being withdrawn from the vagina. Paper tubes, on the other hand, also have problems. Commercially available cardboard tubes for tampons are generally spirally wound and open at the leading edge which may result in a fiber slough when the tampon is inserted. Such tubes generally have a relatively low beam strength, that is, a low resistance to a radial collapsing of the tube. One example of such spirally wound paper tubes can be found in U.S. Pat. No. 3,764,438, issued Oct. 9, 1973. After the outer tube is formed, the end through which the tampon is ejected may be shaped to have a tapered portion of smaller diameter than the diameter of the tampon. Such tapered portion has a generally round termination with corrugations on slits to form flexible petal portions through which the tampon can be forcibly ejected by the inner telescoping tube. The adhesive for holding the spiral layers together may be water soluble so that the paper tubes may be thrown into a toilet and flushed into the drain pipe. The water soluble adhesive causes delamination of the spiral layers so that the rigid tube structure is quickly softened. The paper is of a type chosen to disintegrate in water. Spirally wound tubes have a relatively low beam strength.

Recent advances in the making of paper tubes by convolutely winding the tubes for greater beam strength are disclosed in U.S. application Ser. No. 446,838 filed Dec. 6, 1982, said application being commonly assigned.

Heretofore, cardboard tampon tubes made from multiple plies of paper have had the same number of plies for both the inner and outer tubes. The outer tube generally requires greater strength and rigidity than the inner tube. Accordingly, when the inner tube has the same number of plies as the outer tube an unnecessary expense is involved.

OBJECTS AND SUMMARY OF THE INVENTION

An object of the invention is to provide a more cost effective tampon applicator by using only a necessary thickness of paper in the inner and outer tubes to give desired strength and rigidity.

A further object of the invention is to reduce the number of plies of paper in one of the inner and outer tubes of a tampon applicator where the tubes are convolutely wound.

Since the outer tube generally requires greater strength and rigidity than the inner pusher tube, because the outer tube must hold the shape of a petal profile on the tip of an end for safety and ease of insertion and not be crushed or distorted when gripped by a user, a 4-ply wrapped tube of approximately 0.012 inch wall thickness is desirable. A 3-ply wrapped tube of approximately 0.009 inch wall thickness is adequate for the inner tube and the elimination of an extra ply is more cost effective.

However, when the tampon applicator is of the type having one or more longitudinal slits through the tube wall to interlock with a projection on the inner wall of the outer tube, a stronger, thicker inner tube is necessary. In this instance, a 4-ply 0.012 inch thick outer tube is used in conjunction with a 5-ply 0.015 inch thick inner tube.

Additional features and advantages of the details of construction of the tampon applicators will become more apparent as the invention is more fully hereinafter described and claimed.

BRIEF DESCRIPTION OF THE DRAWINGS

FIG. 1 is a side elevational view of the telescoping inner and outer tubes;

FIG. 2 shows an enlargement of a portion of the longitudinal cross section of FIG. 1;

FIG. 3 is a side elevational view of a modification of the invention;

FIG. 4a is a perspective view of the inner tube of FIG. 3; and

FIG. 4b is a partial perspective view of the outer tube of FIG. 3.

DETAILED DESCRIPTION OF THE PREFERRED EMBODIMENTS OF THE INVENTION

FIG. 1 shows a tampon applicator having an outer tube 1 for holding a tampon. A petal profile on the tip end 4 restrains the tampon in the tube, but yields to allow the tampon to pass therethrough when pushed by the inner telescoping tube 2. Tubes 1 and 2, preferably, are formed from convolutely wound paper blanks and have a multiple ply thickness. However, it will be appreciated that the tubes may be formed in any suitable manner, i.e., spirally wound, and that any suitable material may be used. The paper blanks have a thickness of approximately 0.003 inch. The plies of the tube are held together by a suitable adhesive, preferably a water soluble heat activatable adhesive.

The outer tube 1 requires greater strength than the inner pusher tube 2 in order to maintain the shape of the petal profile on end 4 and to prevent crushing or distorting of the finger holding section which would increase the force necessary for expulsion of the tampon.

To give the outer tube greater strength an extra ply of paper is added as shown in FIG. 2, wherein outer tube 1 is shown with four plies 3 resulting in a a tube wall thickness of approximately 0.012 inch, and inner tube 2 is formed with three plies resulting in a tube wall thickness of approximately 0.009 inch.

When using a compact applicator of the type shown in FIGS. 3, 5, 4a and 4b, however, the inner tube requires a thicker wall. In this embodiment inner tube 11 has two longitudinal slits 12 and 13. Slit 12 stops short of the ends of the tube and is spaced from the ends of the tube by portions 15. Slit 13 stops short of the inner end of tube 11 by a portion 15 but extends to the outer end of the tube as shown in FIG. 4a. Outer tube 10 is provided with a projection 14 on its inner surface as shown in FIG. 4b. Projection 14 may be formed or attached in any suitable manner, i.e. a punched portion of the tube wall or an adhesively secured portion. Projection 14 interlocks with one of the longitudinal slits to prevent removal of the inner tube from the outer tube. Because the inner tube is slit and has circumferential integrity only through portions 15, a thicker, stronger tube wall is required. In this instance, for example, a 4-ply outer tube having a 0.012 inch wall thickness is used in conjunction with a 5-ply inner tube having a 0.015 inch wall thickness.

In a preferred embodiment, the surfaces of the paper blanks forming the interior of the wound coils of the tubes are coated with a water soluble, heat activatable adhesive. The surfaces of the blanks forming the exterior of the tubes are coated with a thin water soluble thermoplastic such as polyvinyl alcohol, polyvinylpyrrolidone, polyethylene oxide, polyvinyl acetate and hydroxypropyl cellulose to which a high percentage of a suitable clay is mixed to give a smooth slick exterior for ease of insertion and retraction by a consumer. The water soluble heat activatable adhesive may be of any suitable type, but is preferably a composition including polyethyloxazoline, a compatible water dispersible adhesive and an antiblocking agent to prevent premature adhesion. Such composition is more fully described in U.S. Pat. No. 4,522,967.

The number of plies of the formed tube depends on the thickness and strength of the paper used. Preferably, the tubes are formed from paper having a short-fiber, high-ground wood content and a weight of 36–50 lbs. per 1,000 square feet.

Although particular tube structures have been described to illustrate various manners in which tampon applicators can be fabricated and utilized, it will be appreciated that the present invention is not limited to such particular illustrations and descriptions. Accordingly, any and all modifications and equivalent arangements for such devices falling within the scope of the following claims should be considered to be part of the present invention.

I claim:

1. A tampon applicator comprising a larger diameter outer tube adapted to confine a tampon pledget, a smaller diameter inner plunger tube partially telescoped therein and adapted to eject said pledget from said larger diameter tube, said smaller tube having a wall thickness greater than the wall thickness of said larger tube, and said smaller inner tube is provided with at least one longitudinal slit.

2. The tampon applicator of claim 1, wherein said tubes are convolutely wound paper tubes.

3. The tampon applicator of claim 1, wherein said greater diameter tube is provided with a projection on its inner surface to interlock with said at least one longitudinal slit of said smaller diameter tube.

4. The tampon applicator of claim 1 wherein said smaller diameter tube has a wall thickness of four plies and said greater diameter tube has a wall thickness of three plies.

5. The tampon applicator of claim 3 wherein said smaller diameter tube has a wall thickness of four plies and said greater diameter tube has a wall thickness of three plies.

* * * * *